(12) United States Patent
Remacle et al.

(10) Patent No.: US 7,892,818 B2
(45) Date of Patent: Feb. 22, 2011

(54) METHOD AND KIT FOR THE DETERMINATION OF CELLULAR ACTIVATION PROFILES

(75) Inventors: Jose Remacle, Malonne (BE); Patricia Renard, Lonzee (BE); Muriel Art, Namur (BE)

(73) Assignee: Eppendorf Array Technologies S.A., Namur (BE)

( * ) Notice: Subject to any disclaimer, the term of this patent is extended or adjusted under 35 U.S.C. 154(b) by 174 days.

(21) Appl. No.: 12/166,092

(22) Filed: Jul. 1, 2008

(65) Prior Publication Data

US 2009/0082223 A1 Mar. 26, 2009

Related U.S. Application Data

(60) Division of application No. 10/339,161, filed on Jan. 7, 2003, now Pat. No. 7,407,748, which is a continuation-in-part of application No. 09/816,763, filed on Mar. 23, 2001, now Pat. No. 7,396,643.

(30) Foreign Application Priority Data

Mar. 24, 2000 (EP) .................................. 00870057

(51) Int. Cl.
*C12M 1/34* (2006.01)
*C07K 16/00* (2006.01)
(52) U.S. Cl. .................................. 435/287.2; 530/387.1
(58) Field of Classification Search ...................... None
See application file for complete search history.

(56) References Cited

U.S. PATENT DOCUMENTS

| | | | |
|---|---|---|---|
| 4,968,602 A | 11/1990 | Dattagupta | |
| 5,563,036 A | 10/1996 | Peterson et al. | |
| 5,747,253 A | 5/1998 | Ecker et al. | |
| 5,770,722 A | 6/1998 | Lockhart | |
| 5,846,783 A | 12/1998 | Wu et al. | |
| 5,939,261 A | 8/1999 | Loewy et al. | |
| 5,976,795 A | 11/1999 | Voytas | |
| 6,326,489 B1 | 12/2001 | Church et al. | |
| 6,342,353 B1 | 1/2002 | Heslot et al. | |
| 2002/0115198 A1 | 8/2002 | Nerenberg et al. | |

FOREIGN PATENT DOCUMENTS

| | | |
|---|---|---|
| EP | 0620439 A2 | 4/1994 |
| WO | WO 89/11548 | 11/1989 |
| WO | WO 95/30026 | 11/1995 |
| WO | WO 98/03652 | 1/1998 |
| WO | WO 98/08096 | 2/1998 |
| WO | WO 00/22167 | 4/2000 |

OTHER PUBLICATIONS

Kaltschmidt, C. et al. (1995) "Selective recognition of the activated form of transcription factor NF-κB by a monoclonal antibody" *Biol. Chem. Hoppo-Seyler* 376:9-16.

Brand, K. et al. (1996) "Activated transcription factor nuclear factor—kappa b is present in the atherosclerotic lesion," *J. Clin. Invest.* 97:1715-1722.

Baeuerle et al., 1997 "NF-κB as a Frequent Target for Immunosuppressive and Anti-Inflammatory Molecules", *Advances in Immunology*, vol. 65, pp. 111-137.

Ghiorzo, P. et al. (1997) "c-Rel and p65 subunits bind to an upstream NF—κB site in human granulocyte macrophage-colony stimulating factor promoter involved in phorbol ester response in 5637 cells" *FEBS Letters* 418:215-218.

Anthony, et al. (2000) "Rapid diagnosis of bacteremia by universal amplification of 23S ribosomal DNA followed by hybridization to an oligonucleotide array" *J. Clin Microbiol.* 38:781-788.

Guo, et al. (1994) "Direct fluorescence analysis of genetic polymorphisms by hybridization with oligonucleotide arrays on glass supports". *Nucleic Acids Res.* 22:5456-5465.

Zammatteo et al. (1997) "Comparison between microwell and bead supports for the detection of human cytomegalovirus amplicons by sandwich hybridization" *Anal.Biochem.* 253:180-189.

European Search Report from Priority Application EP 00870057, dated Sep. 14, 2000.

Baeuerle et al., 1997 "NF-κB as a Frequent Target for Immunosuppressive and Anti-Inflammatory Molecules". *Advances in Immunology* 65:111-137.

Benotmane et al., 1997 "Nonisotopic Quantitative Analysis of Protein-DNA Interactions at Equilibrium", *Analytical Biochemistry*, 25:181-185.

Bielinska, A. et al, 1990 "Regulation of Gene Expression with Double-Stranded Phosphorothioate Oligonucleotides," *Science* 250:997-1000.

Brivanlou, A. et al., 2002 "Signal Transduction and the Control of Gene Expression," *Science*, 295:813-818.

Ghosh, I. et al., 1999 "Structure-Function Relationship in a E-Sheet Peptide Inhibitor of E47 Dimerization and DNA Binding," *Bioorg. & Med. Chem.* 7:61-66.

Grigoriev, M. et al., 1993 "Inhibition of Gene Expression by Triple Helix-Directed DNA Cross-Linking at Specific Sites" *PNA USA* 90:3501-3505.

Gubler et al.,1995 "Nonradioactive Assay for Sequence-Specific DNA Binding Proteins," *BioTechniques*, 18:1008, 1011-1014.

Nielsen, P. et al., 1991 "Sequence-Selective Recognition of DNA by Strand Displacement with a Thymine-Substituted Polyamide" *Science* 254:1497-1500.

(Continued)

*Primary Examiner*—Kenneth R. Horlick
*Assistant Examiner*—David C Thomas
(74) *Attorney, Agent, or Firm*—Knobbe, Martens, Olson & Bear, LLP

(57) ABSTRACT

A method for obtaining an activation profile of a biological sample by disposing onto a solid support in a pre-determined spatial arrangement a subset of capture molecules able to interact with one or more activated transcription factor(s) present in the biological sample, contacting the biological sample upon the solid support under conditions allowing their interaction, monitoring signals resulting from their interaction, and providing a cellular activation profile from the detected signals.

20 Claims, No Drawings

OTHER PUBLICATIONS

Schreck et al., 1990 The NF-κB transcription factor induces DNA bending which is modulated by its 65-κD subunit, *Nucleic Acids Research*, 18:6497-6502.

Tanaka, H. et al., 1994."Sequence-specific interaction of a β-anomeric double-straded DNA with the p50 subunit of NFIB: application to the decoy approach," *Nucleic Acids Research* 22:3069-3074.

Yao, S. et al., 1998 "Uncoiling c-Jun Coiled Coils: Inhibitory Effects of Truncated Fos Peptides on Jun Dimerization and DNA Binding In Vitro," *Biopolymerics* 47:277-283.

Hibma, M. et al., (1994) A non-radioactive assay for the detection and quantification of a DNA binding protein. *Nucleic Acids Research* 22:3806-3807.

Yi et al., 1999 "Divalent Cations Stimulate Preferential Recognition of a Viral DNA End by HIV-1 Integrase." *Biochemistry*, 38:8458-8468.

Zabel et al., 1993 "Nuclear uptake control of NF-κB by MAD-3, an IκB protein present in the nucleus" *EMBO Journal*, 12:201-211.

SEQUENCE LISTING

<160> NUMBER OF SEQ ID NOS: 27

<210> SEQ ID NO 1
<211> LENGTH: 8
<212> TYPE: DNA
<213> ORGANISM: Artificial Sequence
<220> FEATURE:
<223> OTHER INFORMATION: Transcription factor Ets/Elk-1

<400> SEQUENCE: 1 caggaagt                                                                 8

```
<210> SEQ ID NO 2
<211> LENGTH: 9
<212> TYPE: DNA
<213> ORGANISM: Artificial Sequence
<220> FEATURE:
<223> OTHER INFORMATION: Transcription factor STAT 1/3

<400> SEQUENCE: 2 ttccgggaa                                                                 9

<210> SEQ ID NO 3
<211> LENGTH: 6
<212> TYPE: DNA
<213> ORGANISM: Artificial Sequence
<220> FEATURE:
<223> OTHER INFORMATION: Transcription factor c-Myc

<400> SEQUENCE: 3 cacgtg                                                                    6

<210> SEQ ID NO 4
<211> LENGTH: 7
<212> TYPE: DNA
<213> ORGANISM: Artificial Sequence
<220> FEATURE:
<223> OTHER INFORMATION: Transcription factor c-Jun

<400> SEQUENCE: 4 tgagtca                                                                   7

<210> SEQ ID NO 5
<211> LENGTH: 8
<212> TYPE: DNA
<213> ORGANISM: Artificial Sequence
<220> FEATURE:
<223> OTHER INFORMATION: Transcription factor ATF-2

<400> SEQUENCE: 5 tgacatca                                                                  8

<210> SEQ ID NO 6
<211> LENGTH: 9
<212> TYPE: DNA
<213> ORGANISM: Artificial Sequence
<220> FEATURE:
<223> OTHER INFORMATION: Transcription factor SMAD 4

<400> SEQUENCE: 6 agccagaca                                                                 9

<210> SEQ ID NO 7
<211> LENGTH: 9
<212> TYPE: DNA
<213> ORGANISM: Artificial Sequence
<220> FEATURE:
<223> OTHER INFORMATION: Transcription factor MEF2

<400> SEQUENCE: 7 taaaaataa                                                                 9

<210> SEQ ID NO 8
<211> LENGTH: 13
<212> TYPE: DNA
<213> ORGANISM: Artificial Sequence
<220> FEATURE:
<223> OTHER INFORMATION: Transcription factor PPAR(gamma)
```

```
<400> SEQUENCE: 8
aggtcaaagg tca                                                    13

<210> SEQ ID NO 9
<211> LENGTH: 9
<212> TYPE: DNA
<213> ORGANISM: Artificial Sequence
<220> FEATURE:
<223> OTHER INFORMATION: Transcription factor C/EBP

<400> SEQUENCE: 9 ttgcgcaat                                                          9

<210> SEQ ID NO 10
<211> LENGTH: 7
<212> TYPE: DNA
<213> ORGANISM: Artificial Sequence
<220> FEATURE:
<223> OTHER INFORMATION: Transcription factor CbfaI

<400> SEQUENCE: 10 aaccaca                                                            7

<210> SEQ ID NO 11
<211> LENGTH: 6
<212> TYPE: DNA
<213> ORGANISM: Artificial Sequence
<220> FEATURE:
<223> OTHER INFORMATION: Transcription factor MyoD

<400> SEQUENCE: 11 cacctg                                                             6

<210> SEQ ID NO 12
<211> LENGTH: 8
<212> TYPE: DNA
<213> ORGANISM: Artificial Sequence
<220> FEATURE:
<223> OTHER INFORMATION: Transcription factor Oct 4

<400> SEQUENCE: 12 atttgcat                                                           8

<210> SEQ ID NO 13
<211> LENGTH: 10
<212> TYPE: DNA
<213> ORGANISM: Artificial Sequence
<220> FEATURE:
<223> OTHER INFORMATION: Transcription factor E2F

<400> SEQUENCE: 13
taggcgcgaa                                                        10

<210> SEQ ID NO 14
<211> LENGTH: 19
<212> TYPE: DNA
<213> ORGANISM: Artificial Sequence
<220> FEATURE:
<223> OTHER INFORMATION: Transcription factor p53

<400> SEQUENCE: 14
ggacatgccc gggcatgtc                                              19

<210> SEQ ID NO 15
<211> LENGTH: 10
```

```
<212> TYPE: DNA
<213> ORGANISM: Artificial Sequence
<220> FEATURE:
<223> OTHER INFORMATION: Transcription factor NFkB

<400> SEQUENCE: 15
gggactttcc                                                          10

<210> SEQ ID NO 16
<211> LENGTH: 8
<212> TYPE: DNA
<213> ORGANISM: Artificial Sequence
<220> FEATURE:
<223> OTHER INFORMATION: Transcription factor CREB

<400> SEQUENCE: 16 tgacgtca                                                             8

<210> SEQ ID NO 17
<211> LENGTH: 10
<212> TYPE: DNA
<213> ORGANISM: Artificial Sequence
<220> FEATURE:
<223> OTHER INFORMATION: Transcription factor SP1

<400> SEQUENCE: 17
ggggcggggc                                                          10

<210> SEQ ID NO 18
<211> LENGTH: 12
<212> TYPE: DNA
<213> ORGANISM: Artificial Sequence
<220> FEATURE:
<223> OTHER INFORMATION: Transcription factor NFAT

<400> SEQUENCE: 18
gaggaaaatt tg                                                       12

<210> SEQ ID NO 19
<211> LENGTH: 15
<212> TYPE: DNA
<213> ORGANISM: Artificial Sequence
<220> FEATURE:
<223> OTHER INFORMATION: Transcription factor ER

<400> SEQUENCE: 19
aggtcacagt gacct                                                    15

<210> SEQ ID NO 20
<211> LENGTH: 13
<212> TYPE: DNA
<213> ORGANISM: Artificial Sequence
<220> FEATURE:
<223> OTHER INFORMATION: Transcription factor HNF1

<400> SEQUENCE: 20
gttaatgatt aac                                                      13

<210> SEQ ID NO 21
<211> LENGTH: 11
<212> TYPE: DNA
<213> ORGANISM: Artificial Sequence
<220> FEATURE:
<223> OTHER INFORMATION: Transcription factor HNF3

<400> SEQUENCE: 21
```

-continued

```
tattgactta g                                                                11

<210> SEQ ID NO 22
<211> LENGTH: 9
<212> TYPE: DNA
<213> ORGANISM: Artificial Sequence
<220> FEATURE:
<223> OTHER INFORMATION: Transcription factor HNF4

<400> SEQUENCE: 22 tggacttag                                                                    9

<210> SEQ ID NO 23
<211> LENGTH: 10
<212> TYPE: DNA
<213> ORGANISM: Artificial Sequence
<220> FEATURE:
<223> OTHER INFORMATION: Transcription factor HNF6

<400> SEQUENCE: 23
atattgattt                                                                  10

<210> SEQ ID NO 24
<211> LENGTH: 8
<212> TYPE: DNA
<213> ORGANISM: Artificial Sequence
<220> FEATURE:
<223> OTHER INFORMATION: Transcription factor DBP

<400> SEQUENCE: 24 tgatttgt                                                                     8

<210> SEQ ID NO 25
<211> LENGTH: 10
<212> TYPE: DNA
<213> ORGANISM: Artificial Sequence
<220> FEATURE:
<223> OTHER INFORMATION: NFkB binding site

<400> SEQUENCE: 25
gggacttccc                                                                  10

<210> SEQ ID NO 26
<211> LENGTH: 16
<212> TYPE: DNA
<213> ORGANISM: Artificial Sequence
<220> FEATURE:
<223> OTHER INFORMATION: oligonucleotide

<400> SEQUENCE: 26
gaaggggggg gaggga                                                           16

<210> SEQ ID NO 27
<211> LENGTH: 16
<212> TYPE: DNA
<213> ORGANISM: Artificial Sequence
<220> FEATURE:
<223> OTHER INFORMATION: oligonucleotide

<400> SEQUENCE: 27
gggaggaagg ggaggg                                                           16
```

METHOD AND KIT FOR THE DETERMINATION OF CELLULAR ACTIVATION PROFILES

RELATED APPLICATIONS

This application is a divisional of U.S. patent application Ser. No. 10/339,161, filed Jan. 7, 2003, which is a continuation-in-part of U.S. patent application Ser. No. 09/816,763, filed Mar. 23, 2001, which claims priority to European Application No. 00870057.7, filed Mar. 24, 2000, the disclosures of which are incorporated herein by reference in their entireties.

FIELD OF THE INVENTION

The present invention relates to a method and kit for identifying activated transduction cascades in a cell or cell lysate, and obtaining from them a cellular activation profile.

BACKGROUND OF THE INVENTION

The transcriptional activation of eukaryotic genes is a highly regulated process, where a large number of proteins must act in concert to ensure the correct spatio-temporal expression of genes. Transcription factors are key players in this control, as they represent the ultimate regulators of signal transduction cascades. They are subject to a strong regulatory control by cells, since they give to the cells of particular tissues a specific proliferative or differentiated state, and allow that they may adapt and react to a modified environment or stimulus.

The response of a cell to a given condition often results in the stimulation of many regulatory networks, and hence the activation or repression of multiple transcription factors. It is generally admitted that it is the co-ordination of all resulting signals rather than their individual effect that leads to the highly specific pattern of gene expression dictating the cellular response to the initial stimulus. Deciphering the components of these regulatory networks is of particular interest if one aims to better understand, and hence be able to manipulate the expression of the genome.

It is however not an easy task, as some transduction cascades can parallel each other, be interconnected, or exhibit compensatory effects.

There is therefore a need for methods allowing to get a global picture of a cellular activation profile in different stress conditions, through the simultaneous monitoring of a high number of intracellular signals. Such methods would produce large datasets of cellular activation profiles, which might be particularly useful in the drug discovery and development programs. They would indeed help predicting the global effects of yet uncharacterised test molecules, highlight early in the development process unexpected side effects, and enable the identification of the main cellular targets. Comparing the activation profiles of cells following different drug treatments could help classifying those drugs, and identify cellular components whose manipulation might potentate drug effects.

A classification of transcription factors based on their function within cellular regulatory circuits has been recently established by Brivanlou and Darnell (Brivanlou A. H. and Darnell J. E. Science 295, 813-818, 2002). As shown in table 1, transcription factors are divided into constitutively active and regulatory factors, the former being present in the cell nucleus of all cells while the latter are produced in a cell- and time-specific manner. The regulatory factors are composed of developmental and signal-dependent transcription factors, the latter requiring an appropriate stimuli to become transcriptionally active. These signal-dependent transcription factors are divided into steroid receptors, factors activated by internal signals, and factors activated by cell surface receptor-ligand interactions. This last family is composed of factors present in the nucleus or in the cytoplasm, which become transcriptionally active upon stimulation. This is accompanied by a cytoplasm-to-nucleus translocation for the factors retained in the cytoplasm in a latent, inactive form. This 'functional' classification therefore reflects the connection between extracellular signals and the regulation of transcription in eukaryotic cells. It differs from the classical 'structural' classification, where transcription factors are grouped based on the structure of their DNA binding motif

TABLE 1 classification of transcription factors on a functional basis according to Brivanlou and Darnell. Families and examples of transcription factors belonging to each family are presented. The list of transcription factors is not exhaustive, and is presented for illustration purposes only.

| | | regulatory | | | |
|---|---|---|---|---|---|
| | | | signal-dependent | | |
| | | | | | external signals |
| | | steroid | internal | receptor-ligand interactions | |
| constitutive | developmental | receptors | signals | resident nuclear | latent cytoplasmic |
| Sp1 | GATAs | GR | SREBP | Ets/Elk-1 | STATs |
| CCAAT | HNFs | ER | p53 | CREB | SMADs |
| NF1 | Pit 1 | PR | | ATF-2 | NFκB |
| | MyoD | TR | | ATMs | Rel |
| | Myf5 | RARs | | SRF | CI/GLI |
| | Bicold | RXRs | | FOS | NOTCH |
| | Hox | PPARs | | JUN | TUBBY |
| | Forkhead | | | MEF2 | NFATs |
| | Cbfal | | | | |
| | DBP | | | | |

Transcription factors have been implicated in several human diseases, since they control the expression of genes (some being "protective" or "defensive" and others being responsible for secondary deleterious effects). The regulation of the transcription factors may vary with age or may be altered in pathological situations explaining their effects in diseases such as chronic diseases. Furthermore, the dysfunction of a single factor may modify the expression of several genes and affect dozens of different cell types. Molecular characterization of these altered transcription factors, especially regarding their activity or their interaction with other members of the activation pathway and with the transcriptional initiation complex is therefore of crucial importance to understand their role in a defined pathology and associate them with the pathology. Establishing cell activation patterns based on transcription factor profiling is therefore also of interest to follow disease progression, evaluate the effects of potential treatments, and help identifying the regulatory pathways disrupted.

Establishing the activation profile of a cell through the monitoring of its transcription factor components relies on our ability to discriminate between those factors present in the cell under a resting state, and those rendered transcriptionally active as a result of transduction cascade stimulation. Indeed, the activation of specific transcription factors is largely governed at the post-transcriptional level, and usually depends on post-translational modifications of the factor itself, on its interaction with enzymes or regulatory proteins, or on modifications of its sub cellular localization, the final result being either a stimulation or a repression of one or a series of particular genes.

The most common post-translational modification of transcription factors is phosphorylation/dephosphorylation by kinases/phosphatases, which modulates the DNA-binding capacity, nuclear translocation and/or transcriptional potential of said factors. Protein kinases and phosphatases have been co-purified with transcription factors, suggesting physical association between these proteins. Other modifications have been found of importance for transcription factors activity, such as acetylation, oxidation/reduction, nitrosylation and glycosylation.

Many transcription factors ensure the activation of particular genes through interactions with specific cofactors. As an example, the myogenic basic helix-loop-helix (bHLH) transcription factors direct the expression of their target genes in association with E-proteins such as E12 and MEF2 family members. These protein-protein interactions enhance the activation potential of bHLH transcription factors, and in the case of MyoD and MEF2 cooperativity, the DNA binding of only one of the two partners is required.

Another level of protein-protein interactions mediated by transcription factors connect them to proteins from the basal transcription initiation complex. These can be direct or indirect interactions through cofactors which then interact with the basal complex. This is exemplified by CREB-binding protein (CBP) and the related protein p300, that were found to interact with a growing list of transcription factors. This results in the association of CBP/p300 with components of the basal transcriptional machinery and in the acetylation of histones. It was shown that the intrinsic acetyltransferase activity of these cofactors is also responsible for acetylating the transcription factor itself. CBP/p300, which do not bind DNA by themselves, have therefore emerged as general co-activators, which are recruited by activated transcription factors to the promoter of target genes, where they form a bridge with the basal transcriptional machinery, acetylate histone proteins and transcription factors, and lead to transcriptional activation.

It thus becomes more and more clear that post-translational modifications and protein-protein interactions represent key events in the activation of transcription factors and the control of gene expression. There is therefore intense interest in being able to identify the binding partners of transcription factors and assay their activity. Other proteins exert an important regulation on the transcriptional activation through their DNA or protein interactions, such as histone acetylases, deacetylases, methylases, and chromatin remodelers. It is therefore also of interest to develop methods aimed at detecting and quantifying factors, enzymes and compounds controlling transcription. Such methods should help in the discovery of drugs that interfere with the transcriptional regulation of genes, which can be deregulated in many disorders, and improve the diagnostic of such pathologies through the detection of modifications in the activated state of transcription factors and/or in some of their interactions with protein partners.

The simultaneous assessment of transcription factors present in a transcriptionally active or inactive state, and the building of cellular activation profiles are at the basis of the present invention. The method is amendable to an automated, high throughput format, allowing processing of multiple samples.

STATE OF THE ART

Several methods have been developed to assess the biological activity of individual transcription factors, and identify their binding partners. Current methods include reporter gene assays, gel retardation or EMSA, two-hybrid systems, co-immunoprecipitation and phage display, among others. However, most of these methods are laborious and/or time consuming, preventing the simultaneous analysis of multiple factors from a same sample and the processing of multiple samples, and do not take into account the activation state and/or DNA binding capacity of the transcription factors. The detection of protein partners which associate to a transcription factor only when it is bound to its target DNA sequence, can be performed by EMSA using supershift experiments. This is achieved by contacting the transcription factor, possibly bound to protein partners, with an antibody directed to one of these partners, prior to the addition of a labelled oligonucleotide containing the DNA-binding sequence of the transcription factor. If the protein partner physically interacts with the transcription factor, it will be present in the DNA/transcription factor complex, and this will be visualised through the capacity of the antibody to "supershift" the DNA/transcription factor complex during electrophoresis. This approach is technically difficult, however, and presents the limitations inherent to the EMSA technology.

Identifying the activated state of a transcription factor remains very challenging. There is no simple and direct method to assay the activity of transcription factors or other DNA-bound proteins especially using colorimetric methods, which can be adapted to high-throughput screening and enable the development of new compounds affecting the biological activity of these factors (including enzymes). The document WO 00/22167 describes a method for detecting the activity of a transcription factor by a "DNA-nicking assay". Said method is based on the discovery that certain transcription factors activate transcription by creating DNA nicks in one of the strands of their target template. Detecting DNA nicks or DNA nicking activity is therefore used to assess the activation potential of a transcription factor. Such assays are adapted to a "DNA chip" to allow rapid screening and identification of transcription factors activity wherein DNA oligonucleotides or fragments containing the sequence recognised by the transcription factor(s) are bounded to a matrix which is utilised as a support to identify those sequences, that are cleaved in any solution containing the corresponding transcription factor(s).

The document WO 98/03652 describes the acetylation of compounds involved in the transcriptional machinery and a protein called P/CAF which binds to CBP/p300 and can, under reducing conditions and specific binding conditions, acetylate histones. The screening method is based upon the modulation of the histone acetylation potential of P/CAF and CBP/p300 and of the binding of DNA-binding transcription factors to CBP/p300. However said document neither mentions nor suggests the use of a solid support for the assay of transcription factors binding or the use of transcription factors acetylation as a criteria to assess their activation status.

AIMS OF THE INVENTION

The present invention aims to provide a new method and device (kit) for detecting the activation state of transcription factors affecting the direct or indirect stimulation or repression of genetic sequences.

One particular aim of the invention is to provide a method and device for obtaining an activation profile of a cell by simultaneously detecting the activation state of its transcription factor components.

DEFINITIONS

"Transcription factors" are proteins which bind to specific nucleotide sequences of double-stranded DNA, whose activation (either by themselves or with the help of other proteins) will influence the transcription of DNA.

"Transcription factors" are often found in both active and inactive forms, the shift from one form to the other being usually reversible. The activation state of transcription factors as described herein is therefore defined as their potential to modulate, either activate or repress, the transcription of genetic sequences.

The "activation profile" of a cell is defined as the status of control of one or more cellular gene expression.

The term "regulatory circuits" refers to the connection of extracellular signalling to the transcriptional regulation of genes. The regulatory circuits as referred to herein are classified according to table 1.

The term "solid support" refers to any material made of elements selected from the group consisting of polymers, glass, metals or silicium; said material being able to fix directly or be covered by a layer able to fix the capture molecules necessary for the transcription factors interaction and assay. The forms of the supports are preferentially, but not limited to, multi-well plates of 96, 384 or 1536 wells, micro-arrays with planar surfaces or with cavities, where the different capture molecules are present in different spots on the micro-arrays, or (possibly magnetic) microbeads for using for their assayed in FACS machines or for facilitating their washing through their magnetic properties.

The term "capture molecule" as used herein refers to a molecule interacting with transcription factors in their activated state, directly or indirectly, or with any other component associated with this activated state.

The term "cofactors" as used herein are molecules binding transcription factors (directly or indirectly) and modulating their transcriptional activation potential. They can be co-activators, co-repressors or other peptides/molecules modulating transcription factor activity.

SUMMARY OF THE INVENTION

The present invention provides a method for obtaining an activation profile of a biological sample (a cell or tissue or an extract of them) by the following steps of:

(a) providing a solid support containing a subset of (possibly different) capture molecules able to interact with one or more (preferably activated) transcription factor(s) in a predetermined spatial arrangement, said transcription factor(s) being present in said biological sample;

(b) contacting the said cell or tissue extract with the solid support under conditions allowing interaction of the capture molecules with the (preferably activated) transcription factors of the cell or tissue, directly or indirectly;

(c) monitoring (detecting and/or quantifying) signals resulting from said interactions and (d) providing a cell or tissue activation profile from said detected signal(s). Said activation profile can be stored in a computer memory or on a computer readable media.

In one embodiment, the solid support contains at least two, preferably at least five unique (or species) (different) capture molecules belonging to the same or to different regulating circuits. In another embodiment, each unique capture molecule is present in duplicate, more preferably in triplicate on the solid support. In yet another embodiment, the subset of capture molecules is selected from a larger set of (different) capture molecules so as to be relevant to the cell or tissue to be studied. In a preferred embodiment, at least one type of capture molecule interacts with the biological sample and allow the generation of a signal.

Advantageously, the activation profile is obtained from the signal(s) generated following a binding upon those capture molecules which have interacted with the transcription factors from the sample; the amount of signal(s) is therefore generally smaller than the amount of capture molecules.

In another embodiment, more than one signal is obtained and resulting from the specific binding upon each capture molecule.

Preferably, the solid support is a glass slide and the capture molecules are present in a micro-array format. In another embodiment, the solid support is a multi-well plate and the different capture molecules are present (bound to the surface of) in different wells of the multi-well plate. In yet another embodiment, the different capture molecules are present in the same well of a multi-well plate.

Advantageously, the capture molecules are double-stranded DNA molecules, single-stranded DNA molecules RNA, PNA, hybrids thereof or polypeptides. In a more preferred embodiment, the polypeptides are antibodies or (a specific hypervariable) fragments thereof. In another preferred embodiment, the polypeptides are cofactors or specific fragments thereof (able to bind said transcription factor).

The invention also provides a method for detecting changes in an activation state of a cell or tissue, wherein the cell or the tissue (or extract thereof) from a test condition is contacted with a solid support containing a subset of said capture molecules, and wherein an activation profile is obtained; this activation profile being compared to that of a similar cell or tissue from a control condition, and the differences in the monitored signals inform about the test treatment performed.

In another embodiment, the control condition is derived from a normal cell, tissue or extract thereof in a resting state and the test condition is derived from a normal cell or tissue or extract in a stimulated state. Stimulation can be performed by addition of any compound, (natural or synthetic) to said cell or tissue or a modification of their environment (pH, temperature, hypoxia, UV radiation, etc.).

In one embodiment, the two subsets of capture molecules contacted with the test and control samples are identical and are present on a same solid support. In a preferred embodiment, the two subsets of capture molecules are present on the same solid support and are processed simultaneously.

The invention also provides a method for comparing the activation state of two biological samples, comprising:

(a) contacting a solid support containing a subset of capture molecules with a first biological sample and creating a first activation profile according to the invention;

(b) contacting a duplicate solid support containing a subset of capture molecules with a second biological sample and creating a second activation profile according to the invention and (c) comparing the two activation profiles.

Preferably, the first biological sample is derived from a normal cell, tissue or extract and the second biological sample is derived from a diseased cell or tissue or extract. Said first and second biological samples can be derived from a cell or tissue at different proliferation stages or derived from a cell or tissue at different differentiation stages.

The two subsets of capture molecules contacted with the two biological samples are preferably present on a same solid support. The two subsets of capture molecules are present on the same solid support and are preferably processed simultaneously.

The invention further relates to a method of generating datasets of cell or tissue activation profiles, wherein a solid support having a plurality of capture molecules (each allowing to detect one or a series of related transcription factors) is put in contact with a cell, tissue or extract, each activated transcription factor bound onto a capture molecule generating a signal, and the pattern of all obtained signals provides a cell activation status. All activation profiles can be recorded and stored and may constitute a database of cell activation profiles.

The invention provides a method for diagnosing a disorder in a mammal patient (including a human patient), said method comprising the steps of:

(a) immobilising onto a solid support in a pre-determined spatial arrangement a set of capture molecules interacting with transcription factors (wherein a subset of capture molecules specifically interacts with transcription factors characteristic of the disorder);

(b) contacting the solid support with a cell, tissue or extract obtained from said patient, wherein the presence of a subset of transcription factors would be indicative of the disorder and (c) measuring the signals obtained and providing from the generated signal(s) a diagnosis of the presence or prevalence of said disorder in said patient.

The invention also provides a method for evaluating the effects of a compound on the activation state of a cell or tissue, wherein a cell or tissue (or an extract thereof) is put into contact with the compound, and wherein the generated activation profile is compared to the generated profile of an untreated cell or tissue. Differences in the two activation profiles inform about the biochemical and pharmaceutical effects of the said compound.

The invention also relates to a method of assigning a transcription factor to a signal transduction pathway, wherein the capture molecules corresponding to transcription factors of individual signalling cascades (regulatory circuit) are located in a defined sector of the solid support above described.

A last aspect of the present invention is related to a database of activation profiles comprising a plurality of records specific of one or more transcription factors interacting with this specific nucleotide sequence. The characteristics and activation profiles of said transcription factors being characterised by the method according to the invention. Said database could be stored on computer readable media or in a computer memory.

DETAILED DESCRIPTION OF THE INVENTION

The invention describes a method for obtaining an activation profile of a biological sample through the simultaneous assessment of its (activated) transcription factors and the measurement of signals generated. Such assay will give the researchers and clinicians an insight into the reaction of cells or tissues to specific experimental conditions (stress induced by modification of pH, temperature, hypoxia, . . . ) or to pathological or biological conditions of a mammal from which said cell or tissue is obtained.

The assay will also give a better view of the effect of compounds on the cellular activation, thus facilitating their screening and selection for possible therapeutic compounds and applications of compounds.

For instance, it is possible to screen compounds which are interacting with the transcription factor upon their binding side (for instance pharmaceutical compounds blocking or enhancing viral transcription of latently infected cells by viral sequences (HIV viruses, HP viruses, etc.).

The biological sample being analysed in this invention can be a cell, a tissue, an extract of cells or tissues, a body fluid or any sample possibly containing activated transcription factors, or lysates thereof.

Activation of transcription factors usually results from modifications of the factors already present in the cell or sample rather than upregulation of the corresponding genes. Biological samples can therefore be tested for specific features of their activated status like specific phosphorylation, methylation, acetylation, nitrosylation and glycosylation of transcription factors.

The biological sample may contain transcription factor(s) and element(s) (such as cofactors) suitable for obtaining the signals associated with the status of activated transcription factors. In one embodiment, signals from activated transcription factors are generated from an addition or increased concentration of the cofactors. In a preferred embodiment, detection and quantification of the cofactors is performed by using antibodies directed against said cofactors. In another preferred embodiment of the invention, signals corresponding to activated transcription factors are generated by a biological assay of their cofactor(s) enzymatic activities. Said enzymatic activities are preferentially characterised by using a colorimetric assay measure or by using fluorescent, bioluminescent, electrochemical, electrical, and/or magnetic detection methods and means.

Preferably, the signals are obtained by enzymatic measure linked to signal transduction pathways. For example, growth factors may stimulate tyrosine kinase receptors and may lead to a cascade of kinase activations resulting in phosphorylation of specific amino acids of c-Jun peptide which then heterodimerises with c-Fos to form the AP-1 complex, acting as a transcription factor and a binding to the sequence 5'-TGA (C/G)TCA-3'. Kinases acting on c-Jun peptide are the JUN kinases, while activation obtained through the phosphorylation of ELK molecule is performed by the ERK MAP kinase.

These kinases are part of two different activation pathways, and can well be characterised (detected and/or quantified) in the present invention.

In particular, activated transcription factors act either as activators or repressors of transcription by interacting with components of the basal transcription initiation complexes. These complexes are macromolecular assemblies of several different proteins which are required for the RNA polymerase II transcription. The binding of at least one of these transcriptional initiation complex proteins to the DNA-bound transcription factor can be detected, quantified and correlated with the transactivation potential of said transcription factor. These transcriptional initiation complex proteins include (but are not limited to) TFIID, TBP, TAFs, TFIIB, TFIIA, TFIIF, TFIIE, TFIIH, PolI molecules.

Detection of the bound proteins, co-factors or features characteristics of the activation of the transcription factors is best performed through the use of specific (monoclonal) antibodies. Said specific antibodies are then detected by the standard methods, the most current one being a calorimetric enzymatic (or non enzymatic) assay or a fluorescence labelling.

Of particular interest is the detection of CBP/p300 molecules which have been found to be associated to many active transcription factors (such as CREB, Smads, p65-p50 . . . ). These proteins will allow the formation of a molecular bridge between transcription factor(s) and the basal proteins of the transcription initiation complex (TBP, TFIID, . . . ), will modify the structure of the chromatin and will exhibit histone acetyltransferase activity. Acetylation of transcription factors by CBP/p300 is used to assess their active state, and a detection is performed directly on the factor fixed to the support-bound capture molecule (preferably detected by using acetylation-specific antibodies).

The method according to the invention allows to screen, select and recover compounds modulating the acetylation of transcription factors. A recent evidence indicates that a dysfunction in the acetylation at the transcriptional level may be a key determinant in cellular pathogenesis and that molecules able to modulate protein acetylation might be of pharmaceutical interest. The present invention also allows to use the acetylated level of transcription factors for diagnostic purposes, as modifications in this acetylation may be associated with disorders.

The method of the invention allows also the screening and the selection of compounds (ligands) which influence (as agonists or antagonists) the interaction between partners involved in transcription factor activity. Natural ligands exist which can act in a synergistic way to enhance partners binding. For example, interaction between PPARδ and RXRa molecule is potentiated by thrazolidinedione compounds, by fatty acid, by licosomoides or by 9-bis retinoic acid. The method of the present invention is well suited to use transcription factors bound to their capture molecules in order to screen new compounds acting as inhibitors or activators (agonist or antagonist to a binding site) of these factors.

Compounds are incubated with cells and organisms and the cell extracts are tested for specific features of the transcription factor like specific phosphorylation. In a second assay, the influence of these compounds on the interaction of the transcription factor with specific proteins or enzymes is tested. Such interactions are chosen as being specific for the cell activation.

Testing the transcriptional activation potential of a transcription factor can be performed by adding the necessary reagents and enzymes for getting the transcription of DNA (such as the three ribonucleotides needed for the start codon (methionine) and the RNA polymerase). One of said nucleotides can be labelled with a fluorescent dye, so as to detect the synthesised RNA.

The method of the invention allows the detection and identification of abnormal transcription factor(s) function(s) associated with human diseases. This is performed through the creation of cell activation profiles characteristic for the diseases, which are taken as references for subsequent comparisons to cell activation profiles generated from test biological samples.

The method of the invention is especially well adapted for the detection of multiple transcription factors, their binding partners or other DNA-binding proteins on a same support. Micro-array design of capture molecules bound to the support is the preferential embodiment. Each of the transcription factors interacts with a defined capture molecule and signals are measured as described above. In this way, screening, identification and/or quantification of multiple factors or proteins and compounds affecting their activation state is performed, thus increasing the information obtained in one assay. The detection of the different factors from a same sample can also be performed in multi-well plates, where the different capture molecules are present in different wells of the same plate. In a particular embodiment, each row of a plate is dedicated to the assay of one transcription factor.

The use of specific screened compounds like antisense DNA oligonucleotides to inhibit the transcription of genes has been suggested as a possible therapeutic approach for several diseases, and different mechanisms of transcriptional control have been proposed. Triple helix-forming oligonucleotides (TFOs, which are single-stranded DNA oligonucleotides) bind to double-stranded DNA sequences and are expected to block transcription either by inhibiting transcription factor binding or by directly acting as transcriptional repressors (Grigoriev et al., 1993, Proc Natl Acad Sci USA 90, 3501-3505). The single-stranded oligonucleotides hybridise to complementary DNA sequences in a sequence-dependent manner. Double-stranded oligodeoxynucleotides (ODNs), referred to as "decoy" ODNs, can also be used (Bielinska et al., 1990, Science 250:997-1000; Tanaka et al., 1994, Nucleic Acids Res. 22:3069-3074).

These "exogenous" cis elements attenuate the activity of transcription factors through competition for their binding to the endogenous cis elements. Oligonucleotide analogues, where the phosphodiester backbone is replaced with a polyamide to create a 'peptide nucleic acid' or PNA (Nielsen et al., 1991, Science 254:1497-500), can also be used in the present invention. These analogues show high resistance to both nucleases and proteases, and since the polyamide backbone contains no phosphate groups, there is very little repulsion when the PNA hybridises to its target nucleic acid sequence, leading to a more stable complex. PNAs hybridise to complementary sequences of DNA, and PNA:DNA hybridisation is severely affected by base mismatches and PNA can maintain sequence discrimination up to the level of a single mismatch. The screening method is performed in the presence of nucleotides or nucleotide related molecules (such as PNA) which modulate—either stimulate or inhibit—the activity of the transcription factors. Nucleotide related molecules are molecules having a structure similar to the nucleotides and being able to recognise and bind to a particular single- or double-stranded nucleotide sequence. The cell activation profiles in presence and absence of the test cis element are created and compared, and the differences indicate cis element activity.

Most transcription factors exist as oligomers when activated. Disruption of the oligomeric structure could lead to a loss of transcriptional activity, resulting in an inhibition of gene expression. The method of the invention allows to test for the inhibition of the transcription factor-DNA interactions. Disrupting the protein-protein interactions of a multimeric transcription factor would lead to such inhibition. As an example, Ghosh et al. (Bioorg Med Chem, 7:61-6, 1999) have developed a β-sheet peptide which inhibits the dimerization of the transcription factor E47, thereby preventing its binding to DNA. The use of small compounds, such as peptides, to inhibit the assembly of dimeric transcription factors is still in its infancy (Yao et al., 1998, Biopolymers, 47:277-283) but could be speeded up by the present method of the invention.

Another aspect of the present invention is related to a screening, diagnostic and/or quantification kit or device, comprising means and media for performing the method according to the invention.

Preferably, the screening, diagnostic and/or quantification device is a high-throughput screening device, possibly comprising computer-controllable electromagnetic means and robots and other means and media (buffer, washing solution, . . . ) allowing said screening, detection and/or quantification upon any type of solid support surface. The invention also relates to the isolated and characterised compounds able to interact with said transcription factors and modulate their activity.

The present invention will be described in details in the following non limiting examples.

EXAMPLES

Example 1

Single Pathway Micro-Array

The micro-array contains capture molecules interacting with transcription factors of one transduction pathway. This is illustrated for the MAP kinase pathways. The transcription factors to be detected all belong to the those activated following receptor-ligand interaction (see table 1); they are listed in table 2, and the corresponding capture molecules are double-stranded DNA molecules designed to contain the consensus sequences are presented in front of the corresponding factors.

TABLE 2 transcription factors associated to the MAP kinase pathways

| Transcription factor | consensus sequence |
|---|---|
| Ets/Elk-1 | CAGGAAGT (SEQ ID NO: 1) |
| STAT 1/3 | TTCCGGGAA (SEQ ID NO: 2) |
| c-Myc | CACGTG (SEQ ID NO: 3) |
| c-Jun | TGAGTCA (SEQ ID NO: 4) |
| ATF-2 | TGACATCA (SEQ ID NO: 5) |
| SMAD 4 | AGCCAGACA (SEQ ID NO: 6) |
| MEF2 | CTAAAAATAA (SEQ ID NO: 7) |

Step 1: Generation of DNA Capture Molecules

Biotinylated DNA capture molecules are generated by PCR using as a template two annealed oligonucleotides containing a spacer sequence linked to a specific sequence harbouring the consensus DNA binding site for the transcription factor.

Step 2: Spotting on Micro-Arrays

Biotinylated DNA capture molecules at a concentration of 1 µM are spotted in triplicates on streptavidin-coated glass slides, using an adequate spotter. Slides are washed once with $PBS_{50}$ (10 mM phosphate buffer, 50 mM NaCl, p7.4) containing 0.02% Tween20 and once with water, and stored at 4° C. until use.

Step 3: Sample Preparation

To activate the MAPK pathways, Hela cells are induced with PMA and nuclear extracts are prepared as follows, with all steps carried out at 4° C. Control or stimulated cells are washed once with ice-cold PBS (10 mM phosphate buffer, 150 mM NaCl, pH7.4) and once with ice-cold PBS+1 mM $Na_2MoO_4$+5 mM NaF. They are incubated for 3 minutes in ice-cold hypotonic buffer (20 mM Hepes, 5 mM NaF, 1 mM $Na_2MoO_4$, 0.1 mM EDTA, pH 7.9) before addition of Nonidet P40 (0.5% final concentration). Cells are scraped using a rubber policeman and centrifuged 30 seconds at 13000 rpm, 4° C. The pelleted crude nuclei are resuspended in 50 µl ice-cold hypotonic buffer containing 20% glycerol and proteases and phosphatases inhibitors, and an equal volume of the same buffer containing 0.8M NaCl is added. Lysis is performed for 30 minutes at 4° C. under gentle agitation followed by centrifugation for 10 min at 13000 rpm, 4° C. Nuclear extracts are aliquoted from the supernatant and stored at −80° C. The protein content is determined using the Bradford assay.

Samples are prepared by adding 5 µg of nuclear extracts from control or stimulated cells in a total volume of 20 µl lysis buffer (hypotonic buffer containing 20% glycerol, 0.4M NaCl, 1 mM DTT, phosphatases and proteases inhibitors) to 30 µl binding buffer (10 mM Tris/HCl, 50 mM NaCl, 0.5 mM EDTA, 1 mM $MgCl_2$, 4% glycerol, 0.5 mM DTT, 50 µg/ml poly(dI.dC), pH7.5).

Step 4: Assay

Hybridisation chambers are placed around the arrays, samples are added (50 µl/chamber), and incubation is performed for 1 hour under gentle agitation. Slides are washed 3 times with $PBS_{50}$ containing 0.1% Tween20. The primary antibodies directed to the transcription factors to be detected are diluted and mixed in a 800 µl final volume of $PBS_{50}$/1% non fat dry milk. The mix is added to the chambers for 1 hour, and slides are washed 3 times with $PBS_{50}$ containing 0.1% Tween20. A cocktail of secondary antibodies gold-conjugated (800 µl diluted in $PBS_{50}$/1% non fat dry milk) is then added to the chambers for 1 hour, and 4 washing steps with $PBS_{50}$ containing 0.1% Tween20 followed by 2 washing steps with water are performed. Revelation is performed by silver blue reagent (EAT Belgium), and signals are measured. The combination of all signals is used to create the activation profile of non-stimulated and stimulated cells.

Example 2

Multiple Pathways Micro-Array

The micro-array contains molecules interacting with transcription factors from more than one transduction pathway, which are activated or not depending on the cell fate. This is exemplified by transcription factors activated upon mesenchymal stem cells (MSCs) proliferation, differentiation and/or apoptosis. The transcription factors to be detected are listed in table 3, and the corresponding capture molecules are designed to contain the consensus sequences presented in front of the corresponding factors. MSCs can be committed to adipogenesis (activation of PPARγ, C/EBP), osteogenesis (activation of Cbfa1) and myogenesis (activation of MyoD and MEF2) depending on the culture conditions, proliferate (Stat3, E2F activation), stay in an undifferentiated, pluripotent state (Oct4 activation), or turn apoptotic (p53 activation).

TABLE 3 transcription factors associated to mesenchymal stem cells biology

| Transcription factor | consensus sequence |
| --- | --- |
| PPARγ | AGGTCAAAGGTCA (SEQ ID NO: 8) |
| C/EBP | TTGCGCAAT (SEQ ID NO: 9) |
| CbfaI | AACCACA (SEQ ID NO: 10) |
| MyoD | CACCTG (SEQ ID NO: 11) |
| MEF2 | CTAAAAATAA (SEQ ID NO: 7) |
| Stat3 | TTCCGGGAA (SEQ ID NO: 2) |
| Oct4 | ATTTGCAT (SEQ ID NO: 12) |
| E2F | TAGGCGCGAA (SEQ ID NO: 13) |
| p53 | GGACATGCCCGGGCATGTC (SEQ ID NO: 14) |

Capture molecules are generated and spotted on microarrays as described in example 1, and extracts of MSCs grown under different culture conditions and stopped at various time intervals are contacted with the arrays as described above. Signals obtained from each spot are combined and used to create the activation profile of the tested cells.

Example 3

Multi-Well Plates

Multi-well plates are used to analyse the activation of different transcription factors in different wells. Wells from one column are dedicated to the analysis of one transcription factor, and a 96-well plate allows the simultaneous analysis of 12 factors. The factors are listed in table 4.

TABLE 4 transcription factors from major signal transduction pathways

| Transcription factor | consensus sequence |
| --- | --- |
| NFkB | GGGACTTTCC (SEQ ID NO: 15) |
| CREB | TGACGTCA (SEQ ID NO: 16) |

TABLE 4-continued transcription factors from major signal transduction pathways

| Transcription factor | consensus sequence |
| --- | --- |
| Fos/Jun | TGAGTCA (SEQ ID NO: 4) |
| PPAR | AGGTCAAAGGTCA (SEQ ID NO: 8) |
| STAT | TTCCGGGAA (SEQ ID NO: 2) |
| SP1 | GGGGCGGGGC (SEQ ID NO: 17) |
| SMAD | AGCCAGACA (SEQ ID NO: 6) |
| NFAT | GAGGAAAATTTG (SEQ ID NO: 18) |
| Elk1 | CAGGAAGT (SEQ ID NO: 1) |
| ER | AGGTCACAGTGACCT (SEQ ID NO: 19) |
| ATF2 | TGACATCA (SEQ ID NO: 5) |
| cMyc | CACGTG (SEQ ID NO: 3) |

Step 1: Plate Preparation

Four pmoles of biotinylated capture molecules corresponding to each of the 12 selected transcription factors in 50 µl PBS are added to each well of a 96-well plate column coated with streptavidin (Roche). After a one-hour incubation at 37° C., plates are washed twice with 100 µl $PBS_{50}$ containing 0.1% Tween20 and once with 200 µl water, dried and stored at 4° C. until use. The amount of fixed molecule, determined using the PicoGreen assay (Molecular Molecules, OR, USA), is usually around 1 pmole DNA/well.

Step 2: Assay

Five µg nuclear extracts in a total volume of 20 µl lysis buffer are added to 30 µl binding buffer in the DNA-coated multi-wells and incubated 1 hour at room temperature under gentle agitation. Control samples contain 20 µl lysis buffer and 30 µl binding buffer. Wells are washed 3 times with 200 µl $PBS_{50}$/Tween 0.1%.

Detection is performed using primary antibodies specific for the activated state of the transcription factors to be detected. The antibodies are diluted in $PBS_{50}$/1% BSA, and a volume of 100 µl diluted antibody/well are added. Incubation is performed 1 hour at room temperature, and wells are washed 3 times with 200 µl $PBS_{50}$/Tween 0.1%.

A secondary antibody HRP-conjugated is diluted 1000× in $PBS_{50}$/1% non fat dry milk in a final volume of 100 µl, and added to each well for 1 hour at room temperature. Wells are washed 4 times with 200 µl $PBS_{50}$/Tween 0.1%.

Signal measurement is performed by adding 100 µl/well tetramethylbenzidine (Biosource, Belgium) for 10 minutes and 100 µl/well stop solution (Biosource, Belgium), followed by OD measurement at 450 nm. Signals for each activated transcription factor are used to create an activation profile of the cell.

Example 4

Multi-Well Plates

In this example, one well contains the capture molecules of more than one transcription factor. This is illustrated by the combination in each well of the microplate of capture molecules corresponding to liver-enriched transcription factors, listed in table 5. Discrimination between all transcription factors is performed by using different antibodies. Wells from two columns, allowing to process two samples, are incubated with an antibody specific for one transcription factor, according to the general procedure described in example 3. Signals from each column, informing about the activation of one transcription factor in one sample, are used to create cell activation profiles.

TABLE 5

| liver-enriched transcription factors | |
|---|---|
| Transcription factor | consensus sequence |
| HNF1 | GTTAATGATTAAC (SEQ ID NO: 20) |
| HNF3 | TATTGACTTAG (SEQ ID NO: 21) |
| HNF4 | TGGACTTAG (SEQ ID NO: 22) |
| HNF6 | ATATTGATTT (SEQ ID NO: 23) |
| C/EBP | TTGCGCAAT (SEQ ID NO: 9) |
| DBP | TGATTTGT (SEQ ID NO: 24) |

Example 5

Multi-Well Plates to Detect the Effect of Triple-Helix Forming Oligonucleotides on a Cell Activation Profile In this example, a microplate is created with capture molecules for NFκB, detection of the activation potential of the different NFκB members is performed in different wells using specific antibodies, in the presence/absence of the test TFO.

Step 1: Cell Stimulation

SV40 cells are serially cultured in minimal essential medium supplemented with 10% FBS and antibiotics/antimycotics. NFκB induction is performed by stimulating cells with 5 ng/ml interleukin-1 for 30 minutes. Unstimulated cells are taken as a control. Samples are prepared as described above.

Step 2: Plate Preparation; Assay

Assay plates are prepared with a capture molecule harbouring the binding site for NFκB (GGGACTTCCC—SEQ ID NO: 25) as described above. They are incubated with increasing concentrations of a triple-forming oligonucleotide (TFO) with the following sequence:

5'- GAA GGG GGG GGA GGG A-3'   (SEQ ID NO: 26)

This single-stranded purine oligonucleotide binds in an antiparallel orientation to the purine acceptor strand of the double-stranded DNA capture molecule and results in the formation of a triple-helix in which the NFκB binding site is partially blocked. A control hybridisation is performed between the double-stranded DNA capture molecule and increasing concentrations of a control oligonucleotide with the following sequence:

5'- GGG AGG AAG GGG AGG G-3'   (SEQ ID NO: 27)

The single-stranded oligonucleotides are added in 0, 10, 100 and 1000 fold excesses, corresponding respectively to the addition of 0, 10, 100 and 1000 pmoles in buffer 20 mM Tris/HCl, 20 mM $MgCl_2$, 2.5 mM spermidine, pH7.4. Incubation is performed for 1 h at room temperature, following by a washing of the plates with 100 µl/well $PBS_{50}$. 5 µg nuclear extracts in 20 µl lysis buffer and 30 µl binding buffer are then added to the micro-wells as described above, except that both buffers are supplemented with 2 mM $MgCl_2$. Detection is performed using primary antibodies directed to NFκB p50, p65 or c-Rel (4 columns/antibody), and formation of the triple-helix between the capture molecule and the TFO oligonucleotide is assessed by the prevention of NFκB binding to is target sequence when compared to the signals obtained with the control oligonucleotide or with no oligonucleotide. A cellular activation profile is created from untreated and interleukin-1 treated cells without TFO, and used as a reference to which activation profiles obtained in the presence of TFO are compared.

What is claimed is:

1. A screening, diagnostic and/or quantification kit or device for obtaining an activation profile of a biological sample comprising a plurality of transcription factors, said activation profile comprising an activation state of some or all of said transcription factors, said kit or device comprising:

a solid support having on its surface a plurality of different capture molecules present in a predetermined spatial arrangement to form a micro-array able to specifically interact with one or more activated transcription factor(s) present in said biological sample and wherein the different capture molecules are present in different spots on the microarray and wherein the capture molecules contain a double-stranded DNA sequence comprising a specific sequence able to bind activated transcriptional factor(s) and a spacer comprising a double-stranded DNA sequence between about 50 and about 250 base pairs and wherein said double-stranded DNA sequence of between about 50 and about 250 base pairs is not present in said biological sample; and primary antibodies or fragments thereof specific for at least two of the said activated transcriptional factors.

2. The kit or device of claim 1, further comprising labeled secondary antibodies or fragments thereof directed against primary antibodies of the kit or device of claim 1.

3. The kit or device of claim 1, wherein the solid support is a multi-well plate.

4. The kit or device of claim 1, wherein the primary antibodies are directed against a phosphorylated, acetylated or glycosylated form of the activated transcriptional factor(s).

5. The kit or device of claim 1, wherein the primary antibodies are directed against a protein which forms a complex with the transcriptional factor.

6. The kit or device of claim 1, wherein the primary antibodies are directed against a co-factor of the transcriptional factor.

7. The kit or device of claim 2, wherein the label of the secondary labeled antibody is a label for a detection selected from the group consisting of colorimetric, fluorescent, bioluminescent, electrochemical, electrical and/or magnetic detection.

8. The kit or device of claim 1, wherein the double-stranded DNA sequence(s) are covalently bound to the solid support.

9. The kit or device of claim 1, wherein the transcriptional factor is one or more selected from the group consisting of NF-KB, AP-1, Creb, SP-1, C/EBP, GR, HIF-1, Myc, NF-AT, Oct, TBP and CBF-1 or are selected from the factors listed in Table 1.

10. The kit or device of claim 1, wherein the micro-array comprises at least 4 spots/cm$^2$ of solid support surface, each spot containing double stranded DNA sequence(s) for the binding of the transcriptional factor(s).

11. The kit or device of claim 1, wherein the double stranded DNA sequence(s) bound to the solid support surface contain some or all of one or several of the consensus DNA sequences listed in Table 1.

12. The device of claim 1, which is a high-throughput screening device.

13. A screening, diagnostic and/or quantification kit or device of activated transcriptional factors among activated and non-activated transcriptional factors present in a cell or cell lysate, said kit or device comprising:

primary antibodies or fragments thereof specific for the activated transcriptional factors; and either a solid support having bound on its surface a double-stranded DNA sequence(s) bound at a concentration of at least 0.01 pmol/cm$^2$ of said solid support surface, said double stranded DNA sequence(s) comprising a specific sequence able to bind activated transcriptional factor(s) and being linked to the solid support by a spacer comprising a double-stranded DNA sequence between about 50 and about 250 base pairs; or double-stranded DNA sequence(s) comprising a specific sequence able to bind activated transcriptional factor(s) and being linked by a double-stranded DNA spacer sequence of between about 50 and about 250 base pairs to a first member of a binding pair, and a solid support having bound on its surface a second member of the binding pair, wherein the first member is able to interact with the second member.

14. The kit or device of claim 13, further comprising labeled secondary antibodies or fragments thereof directed against the primary antibodies.

15. The kit or device of claim 13, wherein the solid support is a multi-well plate.

16. The kit or device of claim 13, wherein the primary antibodies are directed against a phosphorylated, acetylated or glycosylated form of the activated transcriptional factor(s).

17. The kit or device of claim 14, wherein the label of the labeled secondary antibody is a label for a detection selected from the group consisting of colorimetric, fluorescent, bioluminescent, electrochemical, electrical and/or magnetic detection.

18. The kit or device of claim 13, wherein the transcriptional factor is one or more selected from the group consisting of NF-KB, AP-1, Creb, SP-1, C/EBP, GR, HIF-1, Myc, NF-AT, Oct, TBP and CBF-1, or are selected from the factors listed in Table 1.

19. The kit or device of claim 13, wherein the binding pair is selected from the group consisting of biotin/streptavidin, hapten/receptor and antigen/antibody binding pairs.

20. The device of claim 13, which is a high-throughput screening device.

* * * * *